United States Patent [19]

Stone et al.

[11] Patent Number: 4,869,254

[45] Date of Patent: Sep. 26, 1989

[54] METHOD AND APPARATUS FOR CALCULATING ARTERIAL OXYGEN SATURATION

[75] Inventors: Robert T. Stone, Sunnyvale; Deborah A. Briggs, San Ramon, both of Calif.

[73] Assignee: Nellcor Incorporated, Hayward, Calif.

[21] Appl. No.: 175,115

[22] Filed: Mar. 30, 1988

[51] Int. Cl.$^4$ .................................................. A61B 5/00
[52] U.S. Cl. .................................... 128/633; 128/664; 128/665
[58] Field of Search .................. 128/633, 634, 664–666

[56] References Cited

U.S. PATENT DOCUMENTS

| | | | |
|---|---|---|---|
| 3,412,729 | 11/1968 | Smith, Jr. ........................... | 128/2.05 |
| 3,704,706 | 12/1972 | Herczfeld et al. ................... | 128/2 R |
| 3,994,284 | 11/1976 | Voelker .......................... | 128/2.05 F |
| 3,998,550 | 12/1976 | Konishi et al. ........................ | 356/39 |
| 4,086,915 | 5/1978 | Kofsky ............................. | 128/22 |
| 4,266,554 | 5/1981 | Hamaguri .......................... | 128/633 |
| 4,305,398 | 12/1981 | Sawa ................................. | 128/633 |
| 4,407,290 | 10/1983 | Wilber ............................. | 128/633 |
| 4,545,387 | 10/1985 | Balique ............................ | 128/687 |
| 4,586,513 | 6/1986 | Hamaguri .......................... | 128/633 |
| 4,651,741 | 3/1987 | Passafaro ......................... | 128/633 |
| 4,759,369 | 7/1988 | Taylor ............................. | 128/666 |

FOREIGN PATENT DOCUMENTS 102816  3/1984 European Pat. Off. .
104771  4/1984 European Pat. Off. .
104772  4/1984 European Pat. Off. .
WO86/05674 10/1986 PCT Int'l Appl. .

OTHER PUBLICATIONS

Cohen et al., "Self-Balancing System for Medical and Physiological Instrumentation," IEEE Trans. Bio-Med. Eng., vol. BME-18, p. 66, (1971).

Primary Examiner—Francis Jaworski
Assistant Examiner—John C. Hanley
Attorney, Agent, or Firm—Robert M. Isackson

[57] ABSTRACT

A method and apparatus for improving the calculation of oxygen saturation by non-invasive pulse oximeters during transient conditions. Transient conditions introduce artifactual errors into the detected optical signal because of changes in transmittance of the light with localized blood volume changes and as the average background oxygen saturation level of the patient's blood changes. The invention relates to correcting the detected optical pulses by linear interpolation and rate of change techniques or by selective frequency filtering and compensating the detected optical signal using the filtered signal to provide accurate estimates of oxygen saturation during transient conditions.

17 Claims, 10 Drawing Sheets

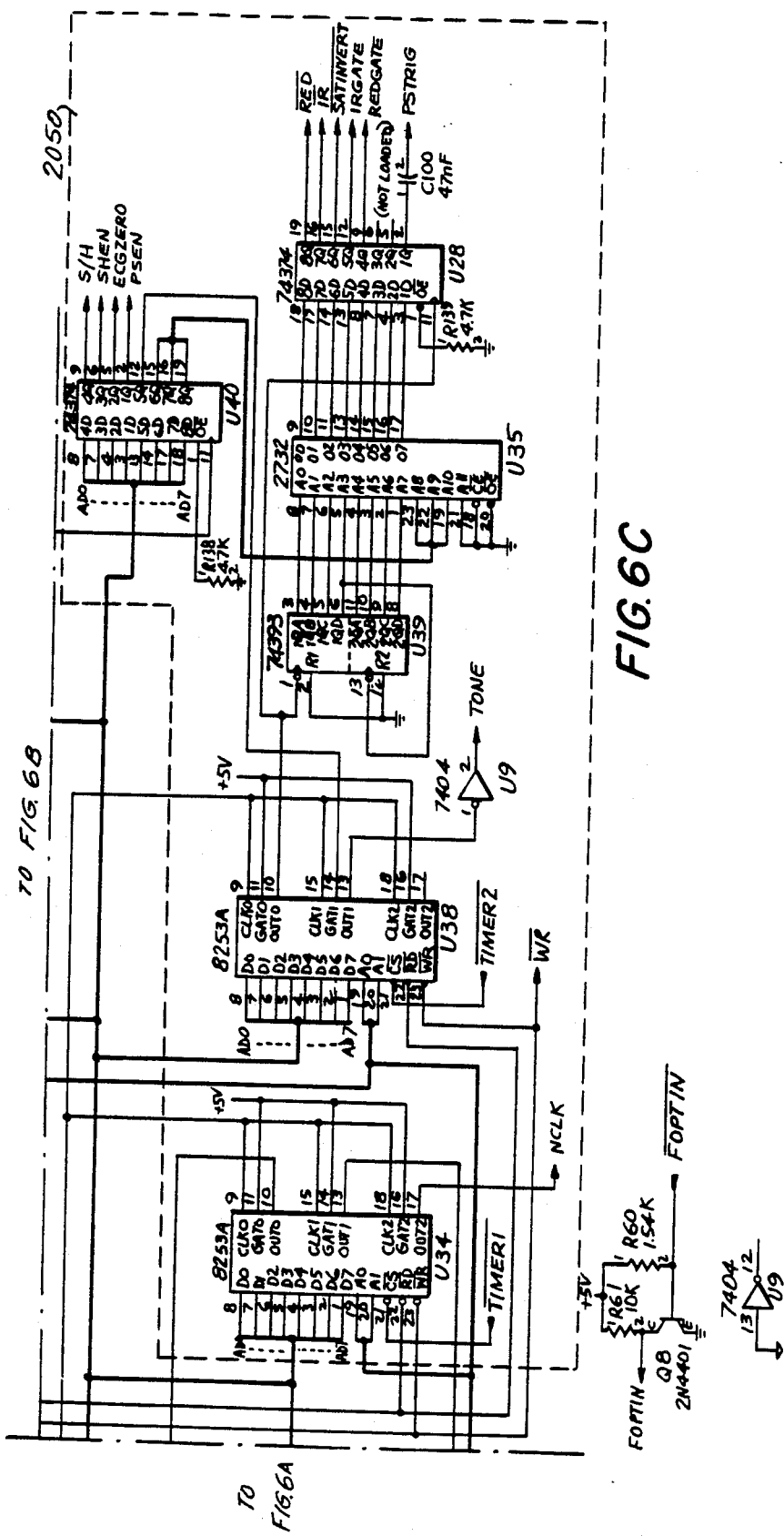

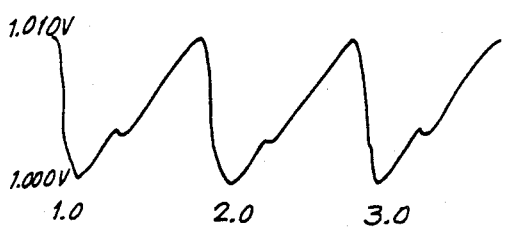
660 nm
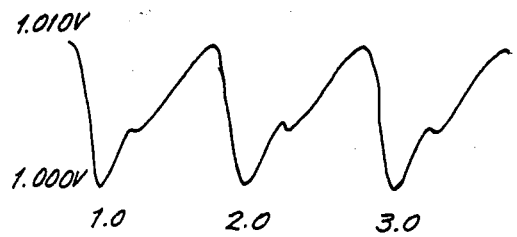
910 nm
I STEADY STATE SATURATION
FIG. 7a
FIG. 7b
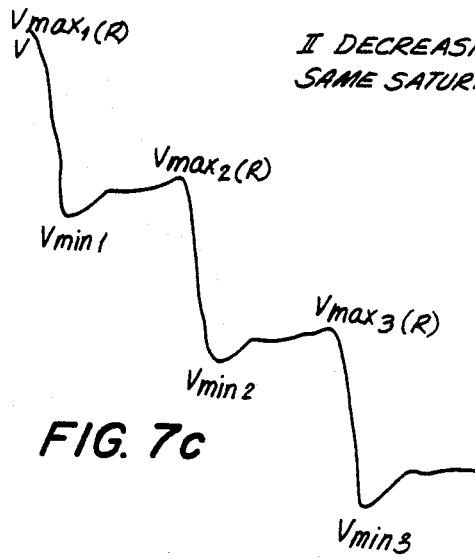
II DECREASING SATURATION, SAME SATURATION AS ABOVE
FIG. 7c
FIG. 7d
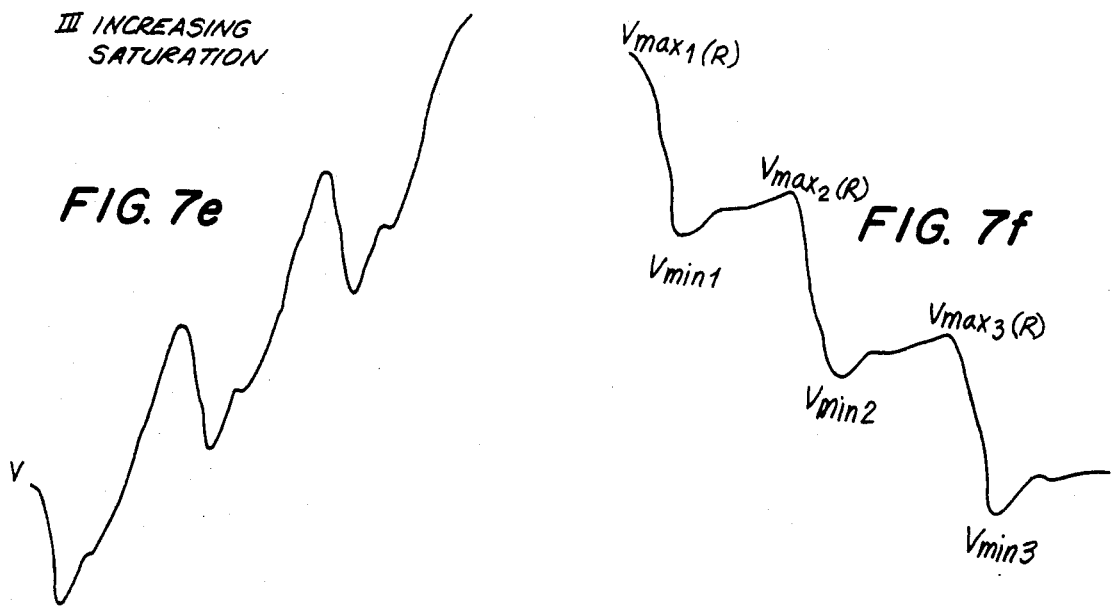
III INCREASING SATURATION
FIG. 7e
FIG. 7f

METHOD AND APPARATUS FOR CALCULATING ARTERIAL OXYGEN SATURATION

This invention relates to non-invasive pulse oximetry and specifically to an improved method and apparatus for calculating arterial saturation during transient conditions based upon photoelectric determination of a patient's plethysmograph. This specification is accompanied by a software appendix.

BACKGROUND OF THE INVENTION

Non-invasive photoelectric pulse oximetry has been previously described in U.S. Pat. Nos. 4,407,290, 4,266,554, 4,086,915, 3,998,550, 3,704,706, European Patent Application No. 102,816 published Mar. 13, 1984, European Patent Application No. 104,772 published Apr. 4, 1984, European Patent Application No. 104,771 published Apr. 4, 1984, and PCT International Publication WO86/05674 published October 9, 1986. Pulse oximeters are commercially available from Nellcor Incorporated, Hayward, Calif., U.S.A., and are known as, for example, Pulse Oximeter Model N-100 (herein "N-100 oximeter") and Model N-200 (herein "N-200 oximeter").

Pulse oximeters typically measure and display various blood flow characteristics including but not limited to blood oxygen saturation of hemoglobin in arterial blood, volume of individual blood pulsations supplying the flesh, and the rate of blood pulsations corresponding to each heartbeat of the patient. The oximeters pass light through human or animal body tissue where blood perfuses the tissue such as a finger, an ear, the nasal septum or the scalp, and photoelectrically sense the absorption of light in the tissue. The amount of light adsorbed is then used to calculate the amount of blood constituent being measured.

The light passed through the tissue is selected to be of one or more wavelengths that is absorbed by the blood in an amount representative of the amount of the blood constituent present in the blood. The amount of transmitted light passed through the tissue will vary in accordance with the changing amount of blood constituent in the tissue and the related light absorption.

For example, the N-100 oximeter is a microprocessor controlled device that measures oxygen saturation of hemoglobin using light from two light emitting diodes ("LED's"), one having a discrete frequency of about 660 nanometers in the red light range and the other having a discrete frequency of about 925 nanometers in the infrared range. The N-100 oximeter microprocessor uses a four-state clock to provide a bipolar drive current for the two LED's so that a positive current pulse drives the infrared LED and a negative current pulse drives the red LED to illuminate alternately the two LED's so that the incident light will pass through, e.g., a fingertip, and the detected o transmitted light will be detected by a single photodetector. The clock uses a high strobing rate, e.g., one thousand five hundred cycles per second, to be easily distinguished from other light sources. The photodetector current changes in response to the red and infrared light transmitted in sequence and is converted to a voltage signal, amplified, and separated by a two-channel synchronous detector—one channel for processing the red light waveform and the other channel for processing the infrared light waveform. The separated signals are filtered to remove the strobing frequency, electrical noise, and ambient noise and then digitized by an analog to digital converter ("ADC"). As used herein, incident light and transmitted light refers to light generated by the LED or other light source, as distinguished from ambient or environmental light.

The light source intensity may be adjusted to accommodate variations among patients' skin color, flesh thickness, hair, blood, and other variants. The light transmitted is thus modulated by the absorption of light in the variants, particularly the arterial blood pulse or pulsatile component, and is referred to as the plethysmograph waveform, or the optical signal. The digital representation of the optical signal is referred to as the digital optical signal. The portion of the digital optical signal that refers to the pulsatile component is labeled the optical pulse.

The detected digital optical signal is processed by the microprocessor of the N-100 oximeter to analyze and identify optical pulses corresponding to arterial pulses and to develop a history as to pulse periodicity, pulse shape, and determined oxygen saturation. The N-100 oximeter microprocessor decides whether or not to accept a detected pulse as corresponding to an arterial pulse by comparing the detected pulse against the pulse history. To be accepted, a detected pulse must meet certain predetermined criteria, for example, the expected size of the pulse, when the pulse is expected to occur, and the expected ratio of the red light to infrared light of the detected optical pulse in accordance with a desired degree of confidence. Identified individual optical pulses accepted for processing are used to compute the oxygen saturation from the ratio of maximum and minimum pulse levels as seen by the red wavelength compared to the maximum and minimum pulse levels as seen by the infrared wavelength, in accordance with the following equation:

$$\text{Saturation} = 100\% \times \frac{BR2 - R(BR1)}{R(BO1 - BR1) + BR2 - BO2}$$

wherein
- BO1 is the extinction coefficient for oxygenated hemoglobin at light wavelength 1 (Infrared)
- BO2 is the extinction coefficient for oxygenated hemoglobin at light wavelength 2 (red)
- BR1 is the extinction coefficient for reduced hemoglobin at light wavelength 1
- BR2 is the extinction coefficient for reduced hemoglobin at light wavelength 2
- light wavelength 1 is infrared light
- light wavelength 2 is red light
- and R is the ratio of the optical density of wavelength 2 to wavelength 1 and is calculated as:

$$R = \frac{\ln[I_{max2}/I_{min2}]}{\ln[I_{max1}/I_{min1}]}$$

wherein
- $I_{max2}$ is the maximum light transmitted at light wavelength 2
- $I_{min2}$ is the minimum light transmitted at light wavelength 2
- $I_{max1}$ is the maximum light transmitted at light wavelength 1
- $I_{min1}$ is the minimum light transmitted at light wavelength 1

The various extinction coefficients are determinable by empirical study as are well known to those of skill in the art. For convenience of calculation, the natural log of the ratios may be calculated by use of the Taylor expansion series for the natural log.

Several alternate methods of processing and interpreting optical signal data have been disclosed in the patents and references cited above.

Normally, the relative oxygen content of the patient's arterial pulses remains about the same from pulse to pulse and the average background absorption between pulses remains about the same. Consequently, the red and infrared light that is transmitted through the pulsatile flow produces a regularly modulated plethysmograph waveform having periodic optical pulses of comparable shape and amplitude and a steady state background transmittance. This regular pulse provides for an accurate determination of the oxygen saturation of the blood based on the detected relative maximum and minimum transmittance of the red and infrared light.

Changes in the patient's local blood volume at the optical detection site affect the absorption of light. These localized changes often result from motion artifact or respiratory artifact which introduce artificial pulses into the blood flow. For example, on each inhalation, the venus return is occluded slightly, which results in the background intensity component of transmittance being decreased due to the relatively larger volume of blood at the optical detection site. Exhalation allows the venus return to expand, thereby decreasing the volume of blood and increasing the background intensity component of transmittance. Consequently, the periodic optical pulses ride on a background intensity component of transmittance that rises and falls with blood volume change. This background intensity component variation, which is not necessarily related to changes in saturation, affects the pulse to pulse uniformity of shape, amplitude and expected ratio of the maximum to minimum transmittance, and can affect the reliability and accuracy of the saturation determination.

In addition, there are times when the patient's background level of oxygen saturation undergoes transient changes, for example, when the patient loses or reacquires oxygen exchange in the lungs while under gaseous anesthesia. Consequently, the detected red and infrared light transmittance changes and the detected plethysmograph waveform rises or falls over time with changes in the average oxygen saturation level in the patient's blood. The transient waveform distorts the pulse shape, amplitude, and the expected ratio of the pulses, which in turn affects the reliability and accuracy of the saturation determination.

Heretofore, with the foregoing known techniques for calculating arterial oxygen saturation, it was known that, during changes in the background intensity absorption component due to artifacts from changes in the patient's blood volume or transient saturation changes, the determined saturation value was not accurate and that it would not become accurate again until the average absorption (or transmittance) level stabilized at the end of the artifact or the saturation transient.

It also was known that saturation calculations based upon transient optical signals provided an over-estimation or under-estimation of the actual saturation value, depending upon the trend. The transmittance of red light near the 660 nanometer wavelength increases as oxygen saturation increases. This results in the detected optical signal value having a smaller pulsatile amplitude, i.e., a smaller relative difference between the maximum and minimum of the pulse. In contrast, the transmittance of the infrared light near the 910 nanometer wavelength decreases as saturation increases, which causes the infrared pulsatile amplitude—relative maximum to minimum—to increase. For both wavelengths, the transmittance changes with changing saturated are substantially linear and continuous in the range of clinical interest, i.e., oxygen saturations between 50% and 100%.

The accuracy of the estimation is of particular concern during rapid desaturation, where average oxygen saturation drops rapidly, but the saturation determination based on the detected optical signals indicates a greater drop than has actually occurred. The determined saturation thus may actuate low limit saturation alarms on an oximeter device that can result in unnecessary and wasteful efforts to resuscitate a patient not in danger.

Applicants believe that the change in transmittance that occurs between the maximum transmittance time and minimum transmittance time is due to the difference in arterial pulsatile length of pulse that has the same oxygen saturation. Because the pulsatile amplitude is quite small, typically less than 5% of the overall intensity change, any small change in overall or background transmittance, such as slight changes in average blood saturation, can have a relatively large effect in the difference in maximum and minimum intensity of the light levels. Because the transmittance effect of changing oxygen saturation is opposite in direction for the red light at 660 nanometers than for infrared light at 910 nanometers, this can result in over-estimation of the pulsatile ratio during periods when saturation is decreasing, and under-estimation during periods when saturation is increasing.

It is therefore an object of this invention to provide a method and apparatus for compensating for the effects of transient conditions in the actual optically detected signal, thereby providing a more accurate estimation of the actual oxygen saturation value.

It is another object of this invention to compensate for the effects of distortion in the detected oxygen saturation signal caused by artifacts due to localized blood volume changes.

It is another object of this invention to compensate for the effects of distortion in the detected oxygen saturation signal caused by transient saturation or blood volume artifact by using a determined rate of change from pulse to pulse, including using interpolation techniques.

It is another object of this invention to compensate for the effects of distortion in the detected oxygen saturation signal caused by transient saturation or blood volume artifact by using the low frequency characteristics of the detected signal values.

SUMMARY OF THE INVENTION

This invention provides a method and apparatus for compensating for the artifactual errors in light transmittance during blood volume changes or transient saturation changes (hereinafter collectively referred to as "transient conditions"), thereby providing for improved accuracy of oxygen saturation calculations during transient conditions. The invention provides apparatus for processing the detected optical signals during transient conditions so that the distortion in transmittance caused by the transient can be compensated. In one embodiment, the compensation is made by converting a transient plethysmograph waveform into a steady state waveform whereby the ratio of the maximum and minimum transmittance can be determined based on the converted waveform and used in making the saturation determination. In an alternate embodiment, the compensation is made by dividing the detected optical signal by its low frequency components, i.e., the background and transient frequencies below the heart beat frequency, from which quotient signal the compensated maximum and minimum transmittance values can be detected and used in making the saturation determination. Throughout this application, the words compensate, correct and adjust are intended to have the same meaning in that the actual detected value is converted to an artificial value that results in a more accurate estimation of the actual oxygen saturation of the patient.

In the preferred embodiment, the detected optical signals are obtained conventionally by passing red and infrared light through a patient's blood perfused tissue, detecting the transmitted light which is modulated by the blood flow, and providing red and infrared detected optical signals that are preferably separately processed and optionally converted from analog to digital signals. The corresponding red and infrared digital optical signals are then processed in accordance with the present invention and the light modulation ratios are determined based on the resulting corrected transmittance pulse and used to calculate oxygen saturation.

In one embodiment, the transient error is corrected by linear interpolation whereby the determined maxima and minima for a first and second optical pulses are obtained, the second pulse following the first and preferably immediately following the first pulse, and the respective rates of change in the transmittance of that wavelength is determined from the maximum transmittance point of the first detected pulse to the second detected pulse. The determined rates of change are then used to compensate any distortion in the detected transmittance of the first detected pulse introduced by the transient in accordance with the following algorithm:

$$V\text{max}(n)^* = V\text{max}(n) - [V\text{max}(n) - V\text{max}(n+1)] \frac{[t\text{max}(n) - t\text{min}(n))]}{[t\text{max}(n+1) - t\text{max}(n)]}$$

where tmax(n) is the time of occurrence of the detected maximum transmittance at the n maximum; tmin(n) is the time of occurrence of the detected minimum transmittance of the wavelength at the n minimum; Vmax(n) is the detected optical signal maximum value at the maximum transmittance of the wavelength at the n maximum; Vmax(n)* is the corrected value, for n being the first optical pulse, and n+1 being the second optical pulse of that wavelength.

By application of the foregoing linear interpolation routine, the detected maximum transmittance value at t=n can be corrected, using the detected values detected at the next coming pulse t=n+1, to correspond to the transmittance value that would be detected as if the pulse were detected at steady state conditions. The corrected maximum value and the detected (uncorrected) minimum value thus provide an adjusted optical pulse maximum and minimum that correspond more closely to the actual oxygen saturation in the patient's blood at that time, notwithstanding the transient condition. Thus, using the adjusted pulse values in place of the detected pulse values in the modulation ratio for calculating oxygen saturation provides a more accurate measure of oxygen saturation than would otherwise be obtained during transient operation.

In the preferred embodiment, the transient error is corrected by linear interpolation whereby the determined maxima and minima for a first and second optical pulses are obtained, the second pulse following the first and preferably immediately following the first pulse, and the respective rates of change in the transmittance of that wavelength is determined from the minimum transmittance point of the first detected pulse to the minimum of the second detected pulse. The determined rates of change are then used to compensate for any distortion in the detected minimum transmittance of the second detected pulse introduced by the transient in accordance with the following algorithm:

$$V\text{min}(n)^* = V\text{min}(n-1) + [V\text{min}(n) - V\text{min}(n-1)] \times \frac{[t\text{max}(n) - t\text{min}(n-1))]}{[t\text{min}(n) - t\text{min}(n-1)]}$$

where tmax(n) is the time of occurence of the detected maximum transmittance at the n maximum; tmin(n) is the time of occurrence of the detected minimum transmittance of the wavelength at the n minimum; Vmin(n) is the detected optical signal minimum value at the minimum transmittance of the wavelength at the n minimum; Vmin(n)* is the corrected value, for n being the second optical pulse, and n−1 being the first optical pulse of that wavelength.

By application of the foregoing linear interpolation routine, the detected minimum transmittance value at t=n can be compensated, using the detected values detected at the preceding pulse t=n−1, to correspond to the transmittance value that would be detected as if the pulse were detected at steady state conditions. The compensated minimum value and the detected (uncompensated) maximum value thus provide an adjusted optical pulse maximum and minimum that correspond more closely to the actual oxygen saturation in the patient's blood at that time, notwithstanding the transient condition. Thus, using the adjusted pulse values in place of the detected pulse values in the modulation ratio for calculating oxygen saturation provides a more accurate measure of oxygen saturation than would otherwise be obtained during transient operation.

As is apparent from the algorithms, during steady state conditions the compensated value is equal to the detected value. Therefore, the linear interpolation routine may be applied to the detected signal at all times, rather than only when transient conditions are detected. Also, the algorithm may be applied to compensate the detected other minimum or maximum transmittance values by appropriate adjustment of the algorithm terms.

The amount of oxygen saturation can be then determined from this adjusted optical pulse signal by determining the relative maxima and minima as compensated for the respective wavelengths and using that information in determining the modulation ratios of the known Lambert-Beers equations. Indeed, the present invention may be applied to any pulsatile flow detected by light absorption or transmittance corresponding to the flow having transient changes or conditions, whether based on the occurrence of individual pulses or averaged pulses.

Applicants also have discovered that the detected optical signals can be processed and corrected in accordance with the present invention by using the frequency characteristics of the detected optical signal. The optical signals for a given wavelength corresponding to the pulsatile arterial blood flow have spectral components including a zero frequency at the background transmittance intensity level, a fundamental frequency at the frequency of the beating heart, and additional harmonic frequencies at multiples of the fundamental frequency. Noise, spurious signals, and motion artifact that appear in the detected optical signal have frequencies that spread across the spectrum. Transient changes to the background transmittance intensity appear as low frequency signals that are below the heart rate frequency.

In accordance with an alternate embodiment of the invention, for each of the wavelengths of the light transmitted, the detected optical signal is split into two portions. For one of the portions, the frequency domain corresponding to the frequency components below the range of the measured heart rate, including the background and any transient frequency components, is separated from the higher frequency components. Applicants have discovered that if the first domain is separated so that no phase shifting occurs relative to the other portion of the unfiltered detected signal, the first domain signal can be divided into the unfiltered signal, thereby to correct for changes in the pulsatile amplitude in the unfiltered signal portion on a continuous basis, for the background transmittance during steady state conditions, during artifactual blood volume changes and transient saturation transmittance changes. It may be appropriate to amplify the separated or filtered signal, the unfiltered signal, or the resulting quotient signal to obtain an adjusted signal having an appropriate amplitude and resolution for making the saturation determination.

Separation of the low frequency components may be realized in either the time domain or the frequency domain. In the time domain, the separation may occur by passing one portion of the analog detected optical signal through conventional electronic circuits such as low pass filters configured to avoid any phase shifting to obtain a filtered signal having only the background and low frequency components, and then passing the filtered signal and a portion of the unfiltered analog detected signal into dividing amplifiers to divide the low passed signal into the unfiltered signal in phase. This process results in a compensated optical signal that can be processed as if it were the actual detected optical signal to determine the relative maxima and minima of the detected pulses for the saturation calculations. Alternately, the detected optical signal may be digitized and processed using digital signal processing techniques to filter the detected signal and divide the filtered signal into the unfiltered detected signal.

Digital processing techniques also may be applied to process the detected optical signal in the frequency domain by the application of well-known Fourier Transforms. In this embodiment, a time-measure of the detected optical signal for a predetermined number of heartbeats is collected and transformed into its spectral components. The frequency components are then separated into two domains, the first domain including spectral components below the measured heart rate so that it includes the zero frequency spectral components of the background intensity and any gradual changes in the background intensity corresponding to the transient condition, and the second domain being above the first so that it includes the spectral components of the fundamental and higher order harmonics of the fundamental for the number of heartbeats in the sample. The separation must occur so that no phase shifting occurs in the first domain. Then, the filtered first domain spectral components can be transformed back into the time domain, into the background and changing background intensity, and divided into the unfiltered detected pulsatile waveform in phase thereby compensating for transient conditions in the unfiltered waveform. As the time-measure is updated to include the patient's current condition, the division of the unfiltered waveform by its low frequency components thus corrects the pulsatile amplitude for changes in the background transmittance on a continuous basis. Thereafter, the oxygen saturation calculation can be based upon the compensated quotient waveform.

Similar to the preferred embodiment, this frequency compensation embodiment may be used all the time.

The apparatus of the preferred embodiment present invention can be used for either time domain or frequency domain transient correction, and includes inputs for the detected optical signals, an analog to digital converter for converting the analog plethysmograph signal to the digital optical signals (unless the plethysmograph signals are provided in digital form), and a digital signal processing section for receiving the digital signals and processing the digital detected optical signal in accordance with one of the foregoing analysis techniques of the present invention, including a for controlling the microprocessor, and display devices.

In its context, the apparatus of the present invention is a part of an oximeter device which has the capability to detect the red and infrared light absorption. In the preferred embodiment, the apparatus of this invention is a part of the Nellcor N-200 oximeter which includes a 16 bit microprocessor manufactured by Intel Corporation, Model No. 8088, software for controlling the microprocessor to perform the operations of the preferred embodiment of the time domain analysis techniques of present invention (in addition to the conventional oximeter functions), and has structure and processing methods that are unrelated to the present invention, and therefore are not discussed herein. The software could be modified to perform the frequency domain analysis techniques of the present invention.

BRIEF DESCRIPTION OF THE DRAWINGS

FIGS. 6A, 6B and 6C are a detailed circuit schematic of the digital signal processing section of FIG. 1.

FIGS. 7a, 7b, 7c, 7d, 7e, and 7f are graphical representations of detected optical signals during steady state and transient conditions.

DETAILED DESCRIPTION OF THE PREFERRED EMBODIMENT

Figure 1:
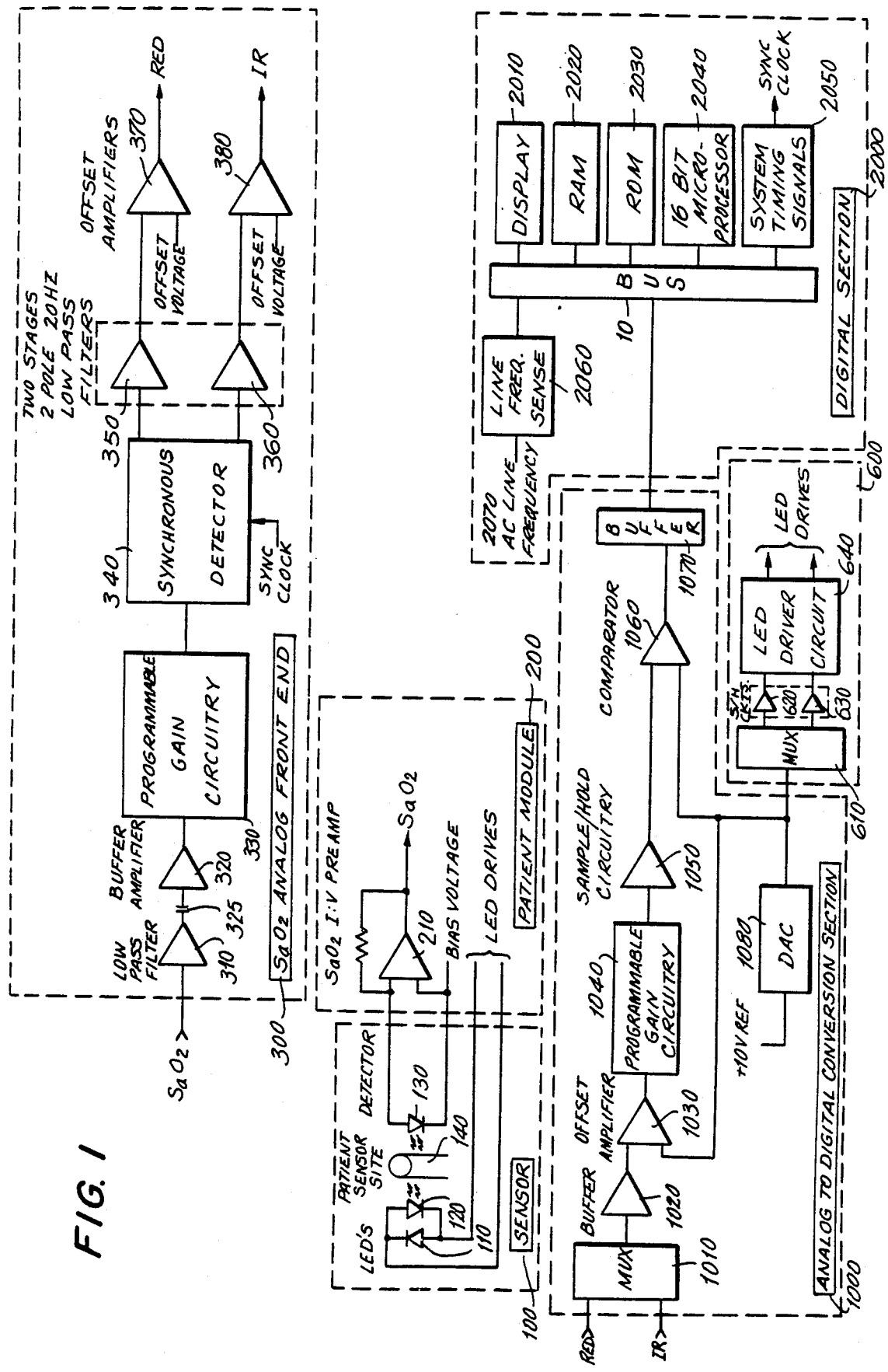
FIG. 1 is a block diagram of the apparatus of this invention and the apparatus associated with the present invention.

Referring to FIG. 1, the preferred embodiment of the present invention relates to the apparatus for processing the detected analog optical plethysmograph signal and comprises portions of analog to digital conversion section ("ADC converter") 1000 and digital signal processing section ("DSP") 2000, including the software for driving microprocessor 2040, which processes the digitized optical signals in accordance with the present invention to determine the oxygen saturation of hemoglobin in arterial blood. Associated with the invention, but not forming a part of the invention, is the apparatus for obtaining the detected analog optical signals from the patient that is part of or is associated with the commercially available Nellcor N-200 Pulse Oximeter. Such apparatus include plethysmograph sensor 100 for detecting optical signals including periodic optical pulses, patient module 200 for interfacing plethysmograph sensor 100 with saturation analog front end circuit 300, and saturation analog circuit 300 for processing the detected optical signals into separate red and infrared channels that can be digitized. The N-200 oximeter also includes LED drive circuit 600 for strobing the red and infrared LEDs in plethysmograph sensor 100 at the proper intensity to obtain a detected optical signal that is acceptable for processing, and various regulated power supplies (not shown) for driving or biasing the associated circuits, as well as ADC 1000 and DSP 2000, from line current or storage batteries.

The associated elements are straightforward circuits providing specified functions which are within the skill of the ordinary engineer to design and build. The associated elements are briefly described here, and reference is made to the corresponding detailed schematics in the Figures and circuit element tables set forth below, to place the apparatus of the present invention in its operating context in the preferred embodiment.

In the preferred embodiment, the invention requires two input signals, the two plethysmograph or detected optical signals at the first and second wavelengths (e.g., red and infrared). More than two wavelengths may be used. If analog signals are provided, they must be within or be adjusted by, for example, offset amplifiers to be within the voltage input range for the ADC. In circumstances where the signals have been digitized already, they must be bit compatible with the digital signal processing devices, DSP.

The plethysmograph signal is obtained in a conventional manner for a non-invasive oximeter, typically by illuminating the patient's tissue with red and infrared light in an alternating fashion, for example, in the manner described above for the N-100 oximeter. Referring to FIG. 1, sensor circuit 100 has red LED 110 and infrared LED 120 connected in parallel, anode to cathode, so that the LED drive current alternately illuminates one LED and then the other LED. Circuit 100 also includes photodetector 130, preferably a photodiode, which detects the level of light transmitted through the patient's tissue, e.g., finger 140, as a single, analog optical signal containing both the red and infrared light plethysmographic, detected optical signal waveforms.

Figure 2:
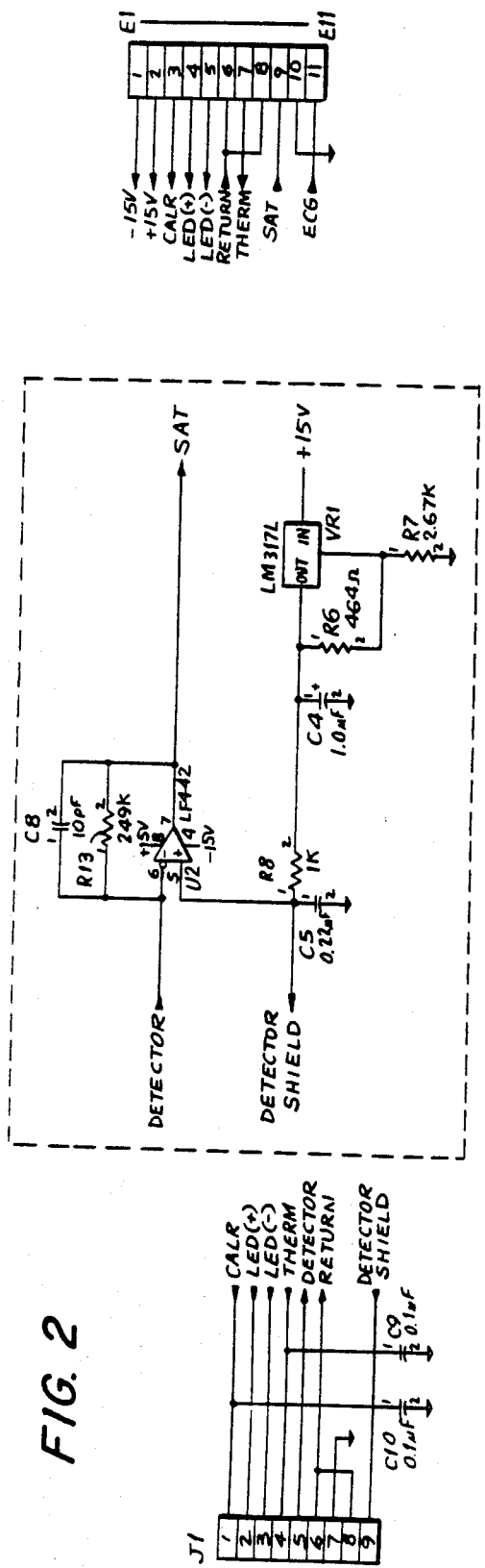
FIG. 2 is a detailed circuit schematic of the saturation preamplifier in the patient module of FIG. 1.

Referring to FIGS. 1, and 2, patient module 200 includes preamplifier 210 for preamplifying the analog detected optical signal of photodetector 130. Preamplifier 210 may be an operational amplifier configured as a current to voltage converter, biased by a positive voltage to extend the dynamic range of the system, thereby converting the photocurrent of photodiode 130 into a usable voltage signal. Patient module 200 also includes leads for passing the LED drive voltages to LEDs 110 and 120.

Figure 3A:
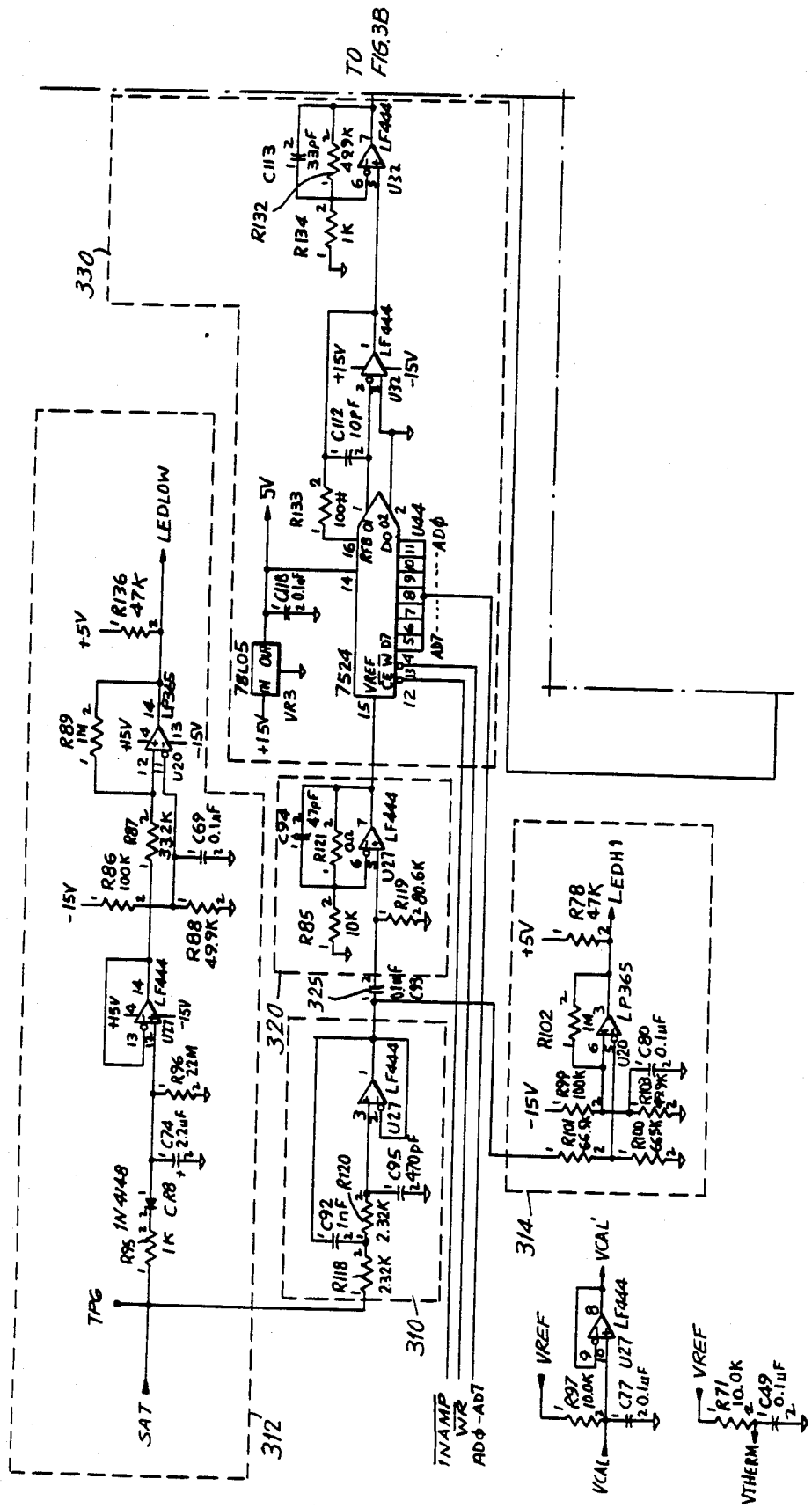
FIGS. 3A and 3B are detailed circuit schematic of the saturation analog front end circuit of FIG. 1.
Figure 3B:
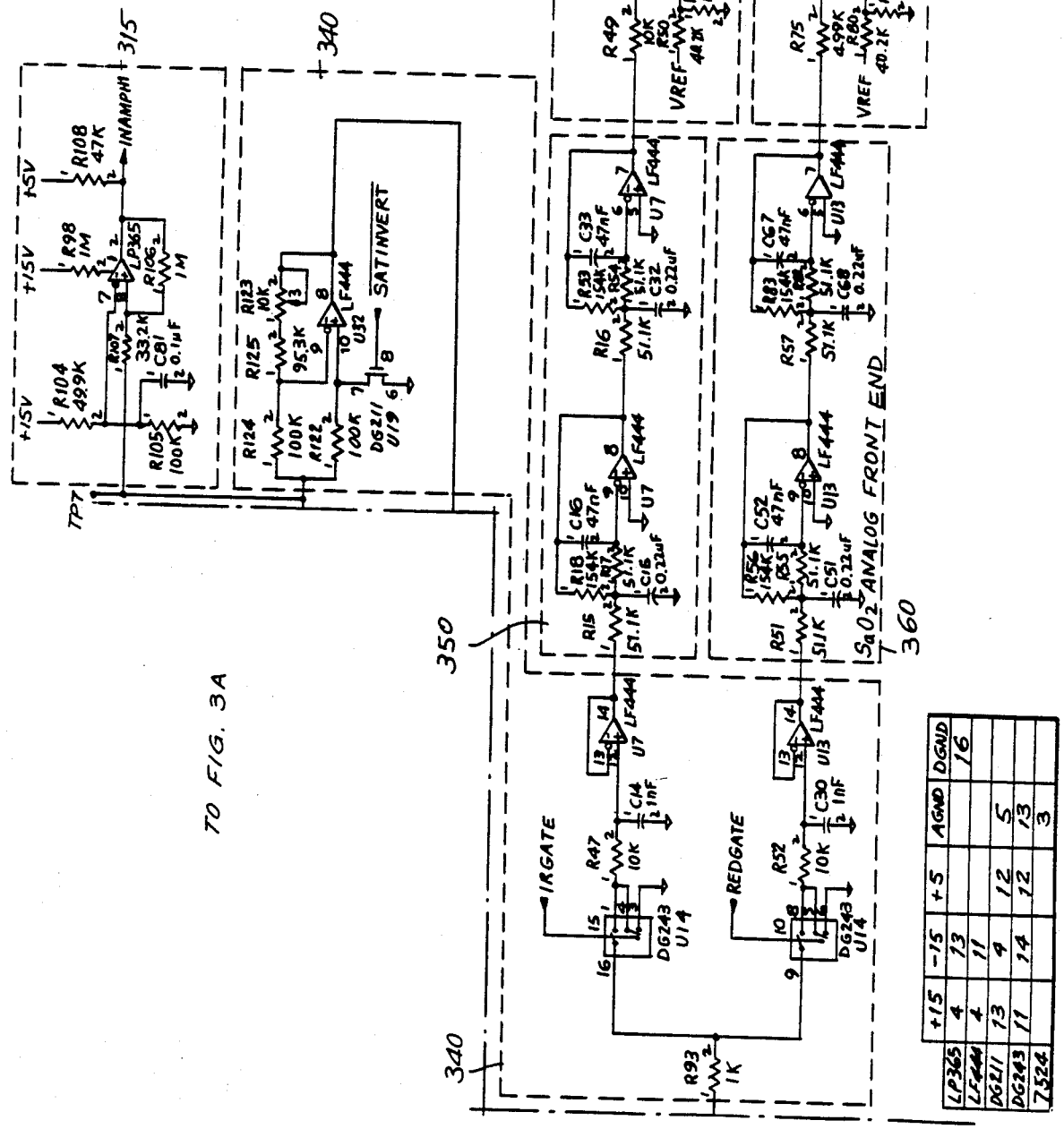

Referring to FIGS. 1, 3A and 3B, saturation analog front end circuit 300 receives the analog optical signal from patient module 200 and filters and processes the detected signal to provide separate red and infrared analog voltage signals corresponding to the detected red and infrared optical pulses. The voltage signal is passed through low pass filter 310 to remove unwanted high frequency components above, for example, 100 khz, AC coupled through capacitor 325 to remove the DC component, passed through high pass filter 320 to remove any unwanted low frequencies below, for example, 20 hertz, and passed through buffer 320 and passed through programmable gain stage 330 to amplify and optimize the signal level presented to synchronous detector 340.

Synchronous detector 340 removes any common mode signals present and splits the time multiplexed optical signal into two channels, one representing the red voltage signals and the other representing the infrared voltage signals. Each signal is then passed through respective filter chains having two 2-pole 20 hertz low pass filters 350 and 360, and offset amplifier 370 and 380. The filtered voltage signals now contain the signal information corresponding to the red and infrared detected optical signals. Additionally, circuits for use in preventing overdriving the amplifiers in saturation circuit 300 may be applied, for example, level-sensing circuits 312 and 314 (located before and after low pass filter 310 respectively) for indicating unacceptable LED drive current, and level sensing circuit 315 (located after programmable gain amplifier 330) for indicating unacceptable input amplifier gain setting.

Figure 5A:
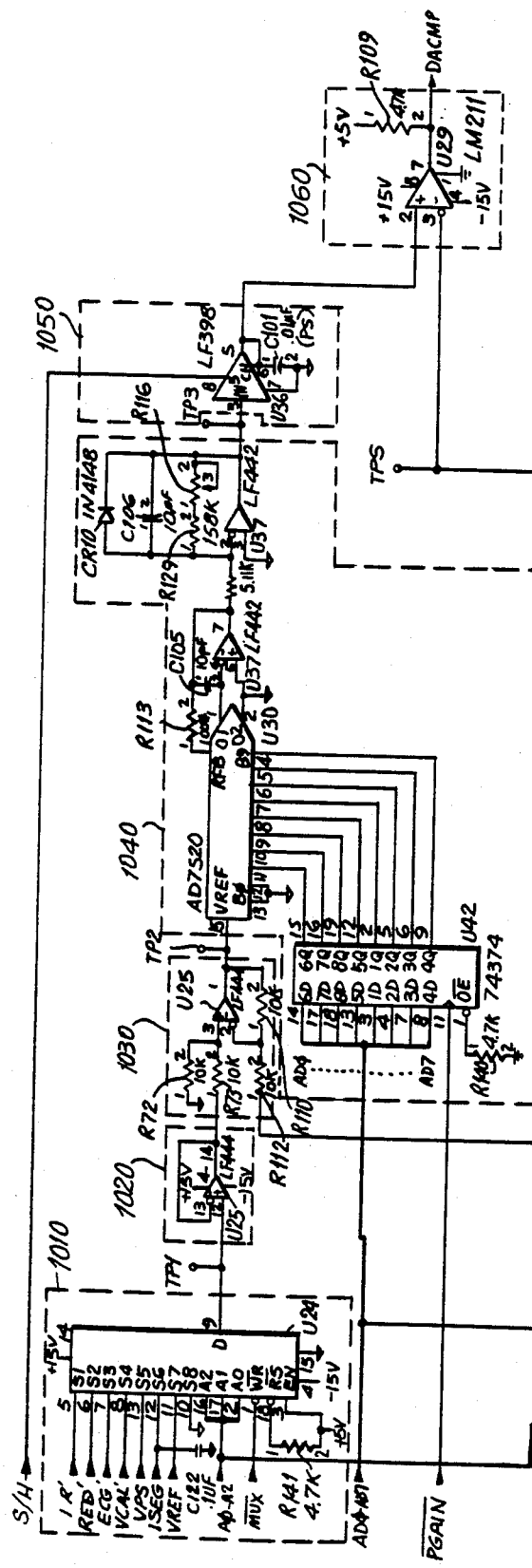
FIGS. 5A and 5B are a detailed circuit schematic of the analog to digital converter section of FIG. 1.
Figure 5B:
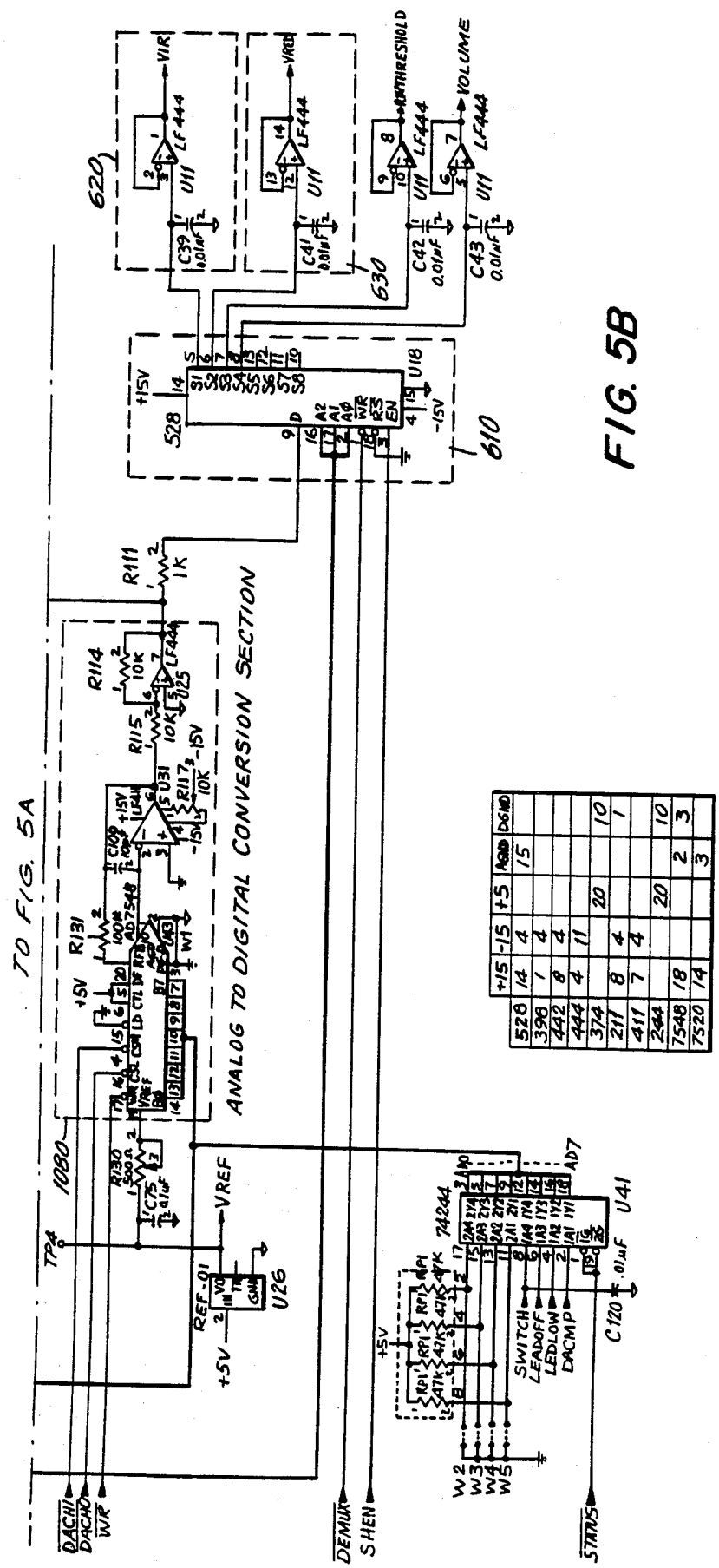
Figure 6A:
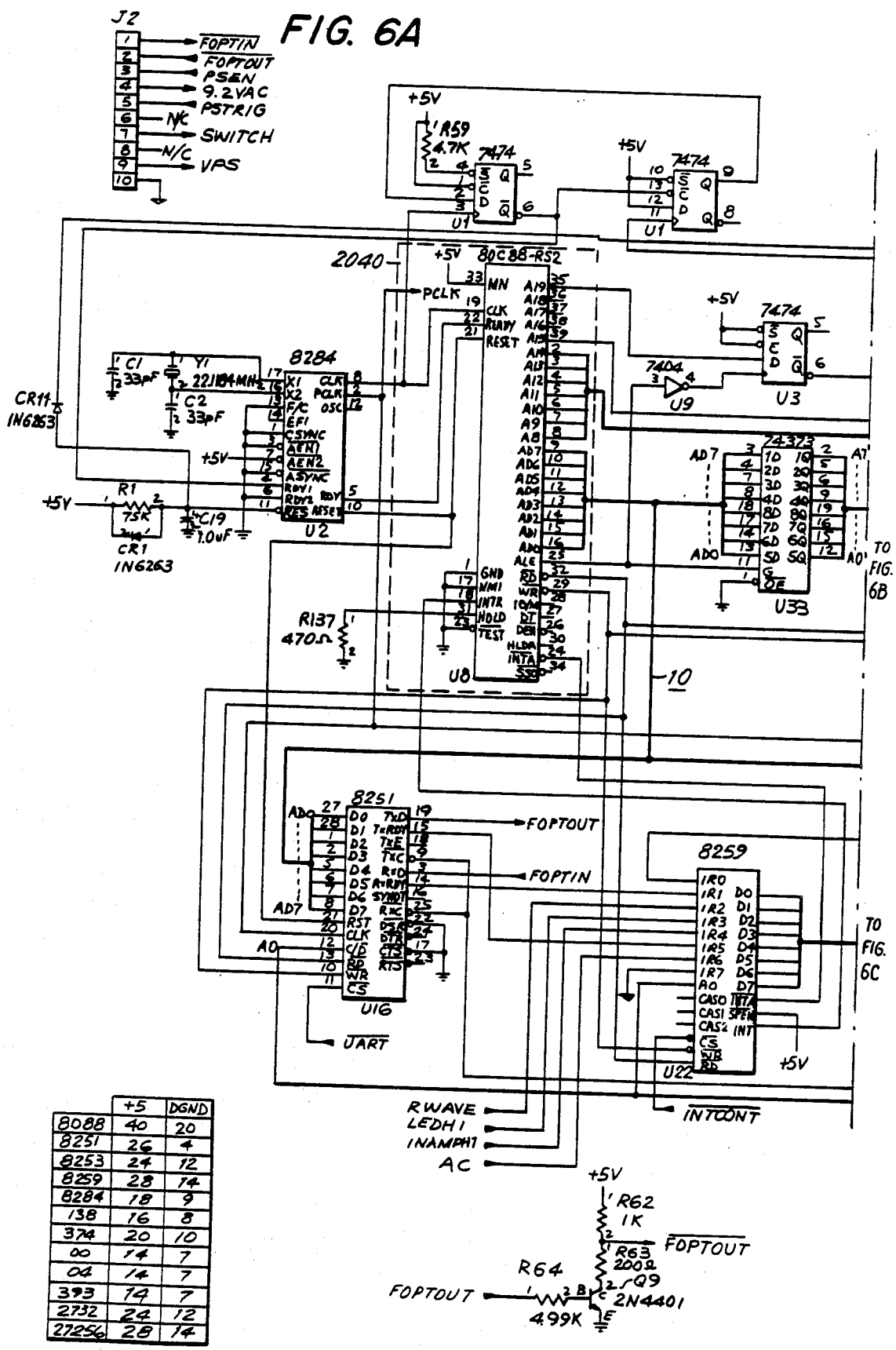
Figure 6B:
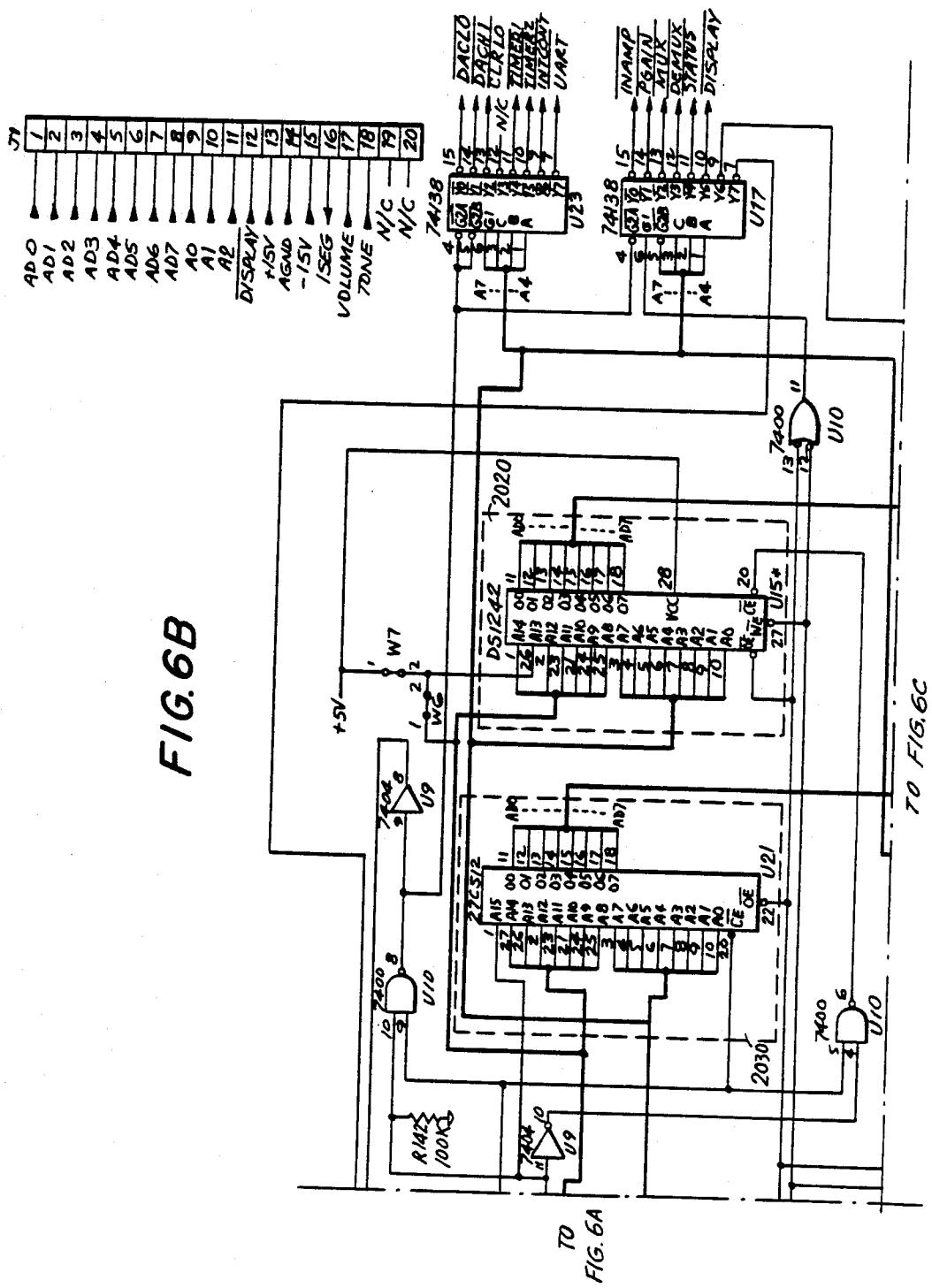

Referring to FIGS. 1, 5A and 5B, ADC 1000 provides the analog to digital conversions required by the N-200 oximeter. The aforementioned two voltage signals, the red detected optical signal and the infrared detected optical signal from patient module 200, are input to ADC 1000. These signals are conventionally multiplexed and digitized by an expanded range 12-bit analog-to-digital conversion technique, yielding 16-bit resolution. The input signals are passed through multiplexer 1010 and buffer amplifier 1020. The converter stage includes offset amplifier 1030 and programmable gain circuitry 1040 which allows a portion of the signal to be removed and the remainder to be further amplified for greater resolution, sample and hold circuit 1050, comparator 1060, and 12-bit digital to analog converter 1080. The buffered signal is passed through offset amplifier 1030 to add a DC bias to the signal wherein a portion of the signal is removed and the balance is amplified by being passed through programmable gain circuitry 1040 to improve the resolution. The amplified signal is then passed through sample and hold circuit 1050, the output of which is fed to one input of comparator 1060. The other input of comparator 1060 is the output of digital to analog ("DAC") converter 1080 so that when the inputs to comparator 1060 are the same, the analog voltage at the sample and hold circuit is given the corresponding digital word in DAC converter 1080 which is then stored in an appropriate memory device as the digitized data for the sample and the next sample is sent to sample and hold circuit 1050 to be digitized.

Referring to FIGS. 1, 4, 5A, 5B, 6A, 6B and 6C, DAC 1080 also generates the sensor LED drive voltages, under the control of microprocessor 2040, using analog multiplexer 610, which separates the incoming analog signal into one of two channels for respectively driving the red and infrared LEDs, having respective sample and hold circuits 620 and 630, and LED driver circuit 640 for converting the respective analog voltage signals into the respective positive and negative bipolar current signals for driving LEDs 110 and 120.

Alternate techniques of converting the analog signals to digital signals could be used, for example, a 16-bit analog to digital converter.

Referring to FIGS. 1, 6A, 6B and 6C, DSP 2000 controls all aspects of the signal processing operation including the signal input and output and intermediate processing. The apparatus includes 16-bit microprocessor 2040 and its associated support circuitry including data bus 10, random access memory (RAM) 2020, read only memory (ROM) 2030, a conventional LED display device 2010 (not described in detail), system timing circuit 2050 for providing the necessary clock synchronizing signals. In the preferred embodiment, microprocessor 2040 is a model 8088 microprocessor, manufactured by Intel Corporation, Santa Clara, California. Alternate microprocessors may be used, such as any of model Nos. 8086, 80186, and 80286, also made by Intel Corporation.

The N-200 oximeter incorporating the present invention is designed to determine the oxygen saturation in one of two modes, an unintegrated mode wherein the oxygen saturation determination is made on the basis of pulses detected in the optical pulse signal that are determined to be optical pulses in accordance with conventional pulse detection techniques, and in an ECG synchronization mode wherein the determination is based on enhanced periodic data obtained by processing the detected optical signal and the ECG waveform of the patient in accordance with an invention that is not a part of the present invention.

The present invention applies to the calculation of saturation based on detecting maximum and minimum transmittance of two or more wavelengths, whether the determination is made pulse by pulse (the unintegrated mode) or based on an averaged or composite pulse that is updated with the occurrence of additional pulses to reflect the patient's actual condition (the ECG synchronized mode).

Interrupt programs control the collection and digitization of incoming optical signal data. As particular events occur, various software flags are raised which transfer operation to various routines that are called from a main loop processing routine.

The detected optical signal waveform is sampled at a rate of 57 samples per second. When the digitized red and infrared signals for a given portion of detected optical signals are obtained, they are stored in a buffer called DATBUF and a software flag indicating the presence of data is set. This set flag calls a routine referred to as MUNCH, which processes each new digitized optical signal waveform sample to identify pairs of maximum and minimum amplitudes corresponding to a pulse. The MUNCH routine first queries whether or not there is ECG synchronization. If there is ECG synchronization, then the MUNCH routine obtains the enhanced composite pulse data in the ECG synchronization mode. Otherwise, MUNCH obtains the red and infrared optical signal sample stored in DATBUF, in the unintegrated mode. The determined maximum and minimum pairs are then sent to a processing routine for processing the pairs. Preferably, conventional techniques are used for evaluating whether a detected pulse pair is acceptable for processing as an arterial pulse and performing the saturation calculation, whether the pulse pair is obtained from DATBUF or from the enhanced composite pulse data.

The MUNCH routine takes the first coming pulse data and determines the maximum and minimum transmittance for each of the red and infrared detected optical signals, takes the second coming pulse data, and determines the relative maximum and minimum transmittance. The routine for processing the pairs applies the aforementioned algorithm to the first and second pulse data of each wavelength and determines the corrected minimum transmittance for the second pulse each wavelength. Then the oxygen saturation can be determined using the corrected minimum and detected maximum transmittance for the second pulses of the red and infrared optical signals.

The application of the present invention and the pair processing routine correction is demonstrated by the following comparative examples, with reference to FIGS. 7a, 7b, 7c, 7d, 7e and 7f and the software appendix.

EXAMPLE I

FIGS. 7a and 7b show representative plethysmograph waveforms for a patient's steady state condition for the red and infrared detected optical signals. $Vmaxr(n)$ equals 1.01 volts, and $Vminr(n)$ equals 1.00 volts, for $n=1,2$, and 3 pulses. $Vmin(n)$ is the detected optical signal minimum value at the minimum transmittance at the n pulse minimum. The modulation ratio for the maxima and minima red signal is $$\frac{Vmaxr(n)}{Vminr(n)} = \frac{1.01v}{1.00v} = 1.01$$

For the infrared wavelength, $Vmaxi(n)=1.01$ v and $Vmini(n)=1.00$ v and the determined modulation ratio also is 1.01.

Using these determined modulation ratios in the formula for calculating the ratio R provides:

$$R = \frac{\ln[Vmaxr(n)/Vminr(n)]}{\ln[Vmaxi(n)/Vmini(n)]} = \frac{.01}{.01} = 1.00$$

A determined $R=1$ corresponds to an actual saturation value of about 81% when incorporated into the aforementioned saturation equation. A saturation of 81% corresponds to a healthy patient experiencing a degree of hypoxia for which some corrective action would be taken.

EXAMPLE II

FIGS. 7c and 7d correspond to representative plethysmographic waveforms for a patient during desaturation or decreasing saturation transient conditions for the red and infrared detected optical signals having optical pulses $n=1, 2,$ and 3. However, in this transient example it is known that at $n=1$, the actual saturation of the patient is very close to that during the steady state conditions in the Example I. In this transient example, the detected values are as follows:

For both the red and infrared signals:

tmax(1)=1.0 secs.
tmin(1)=1.2 secs.
tmax(2)=2.0 secs.
tmin(2)=2.2 secs.
tmax(3)=3.0 secs.
tmin(3)=3.2 secs.

For the red optical signals:
Vmaxr(1)=1.012 v
Vminr(1)=1.000 v
Vmaxr(2)=1.002 v
Vminr(2)=0.990 v
Vmaxr(3)=0.992 v
Vminr(3)=0.980 v For the infrared optical signals:
Vmaxi(1)=1.008 v
Vmini(1)=1.000 v
Vmaxi(2)=1.018
Vmini(2)=1.010 v
Vmaxi(3)=1.028 v
Vmini(3)=1.020 v.

Calculating the oxygen saturation ratio R at n=1, using the detected optical signals provides the following:

$$\begin{aligned} R &= \ln[V\text{maxr}(1)/V\text{minr}(1)]/\ln[V\text{maxi}(1)/V\text{mini}(1)] \\ &= \ln[1.012/1.000]/\ln[1.008/1.000] \\ &= \ln[1.012]/\ln[1.008] \\ &= .012/.008 \\ &= 1.5 \end{aligned}$$

Thus, the determined saturation ratio R of 1.5 based on the detected transmittance corresponds to a calculated oxygen saturation of about 65% for the patient, which corresponds to severe hypoxia in an otherwise healthy patient. This contrasts with the known saturation of about 81% and demonstrates the magnitude of the under-estimation of the oxygen saturation (over-estimation of desaturation) due to the distortion in transmittance of the red and infrared light caused by transient conditions.

Applying the present invention to correct the distorted maximum transmittance point of the detected red optical signal during the transient condition, we find the following:

$$\begin{aligned} V\text{maxr}(1)^* &= V\text{max}(1) - [V\text{max}(1) - V\text{max}(2)] \times \frac{[t\text{max}(1) - t\text{min}(1)]}{[t\text{max}(2) - t\text{max}(1)]} \\ &= 1.012 - [1.012 - 1.002] \times [1.0 - 1.2]/[1.0 - 2.0] \\ &= 1.010 \end{aligned}$$

and correspondingly for the maximum transmittance of the detected infrared optical signal we find:

$$\begin{aligned} V\text{maxi}(1)^* &= 1.008 - [1.008 - 1.018] \times [1.0 - 1.2]/[1.0 - 2.0] \\ &= 1.010 \end{aligned}$$

Thus, by replacing Vmaxr(n) with Vmaxr(n)* and replacing Vmaxi(n) with Vmaxi(n)* in the calculations for determining oxygen saturation ratio R we find:

$$\begin{aligned} R &= \ln[V\text{maxr}(1)^*/V\text{minr}(1)]/\ln[V\text{maxi}(1)^*/V\text{mini}(1)] \\ &= \ln[1.010/1.00]/\ln[1.010/1.00] \\ &= .01/.01 \\ &= 1.0. \end{aligned}$$

Thus, basing the saturation calculations on the corrected maximum transmittance values and the detected minimum transmittance values, the corrected R value corresponds to the same R for the steady state conditions and the actual oxygen saturation of the patient.

EXAMPLE III

FIGS. 7e and 7f correspond to representative plethysmographic waveforms for a patient during increasing saturation transient conditions for the red and infrared detected optical signals having optical pulses n=1, 2, and 3. However, in this transient example it is known that at n=1, the actual saturation of the patient is very close to that during the conditions in the steady state Example I. In this transient example, the detected values are as follows:

For both the red and infrared signals:
tmax(1)=1.0 secs.
tmin(1)=1.2 secs.
tmax(2)=2.0 secs.
tmin(2)=2.2 secs.
tmax(3)=3.0 secs.
tmin(3)=3.2 secs.

For the red optical signals:
Vmaxr(1)=1.008 v
Vminr(1)=1.000 v
Vmaxr(2)=1.018 v
Vminr(2)=1.010 v
Vmaxr(3)=1.028 v
Vminr(3)=1.020 v For the infrared optical signals:
Vmaxi(1)=1.012 v
Vmini(1)=1.000 v
Vmaxi(2)=1.002 v
Vmini(2)=0.990 v
Vmaxi(3)=0.992 v
Vmini(3)=0.980 v.

Calculating the oxygen saturation ratio R at n=1, using the detected optical signals provides the following:

$$\begin{aligned} R &= \ln[V\text{maxr}(1)/V\text{minr}(1)]/\ln[V\text{maxi}(1)/V\text{mini}(1)] \\ &= \ln[1.008/1.000]/\ln[1.012/1.000] \\ &= \ln[1.008]/\ln[1.012] \\ &= .008/.012 \\ &= .667 \end{aligned}$$

Thus, the determined saturation R of 0.667 corresponds to a calculated oxygen saturation of about 95% for the patient which corresponds to a satisfactorily oxygenated patient breathing room air. This contrasts with the known saturation of about 81% and demonstrates the magnitude of the over-estimation of saturation due to the distortion in transmittance of the red and infrared light caused by transient conditions.

Applying the present invention to correct the distorted maximum transmittance point of the detected red optical signal during the transient condition we find:

$$Vmaxr(1)^* = Vmax(1) - [Vmax(1) -$$
$$Vmax(2)] \times \frac{[tmax(1) - tmin(1)]}{[tmax(2) - tmax(1)]}$$
$$= 1.008 - [1.008 - 1.018] \times$$
$$[1.0 - 1.2]/[1.0 - 2.0]$$
$$= 1.010$$

and correspondingly for the detected infrared optical signal:

$$Vmaxi(1)^* = 1.012 - [1.012 - 1.002] \times [1.0 - 1.2]/$$
$$[1.0 - 2.0]$$
$$= 1.010$$

Thus, by replacing Vmaxr(n) with Vmaxr(n)* and replacing Vmaxi(n) with Vmaxi(n)* in the calculations for determining oxygen saturation ratio R we find:

$$R = \ln[Vmaxr(1)^*/Vminr(1)]/\ln[Vmaxi(1)^*/Vmini(1)]$$
$$= \ln[1.010/1.00]/\ln[1.010/1.00]$$
$$= .01/.01$$
$$= 1.0.$$

Thus, basing the saturation calculations on the corrected maximum transmittance values and the detected minimum transmittance values, the corrected R value corresponds to the same R for the steady state conditions and the actual oxygen saturation of the patient.

EXAMPLE IV

FIGS. 7c and 7d also correspond to representative plethysmographic waveforms for a patient during desaturation or decreasing saturation transient conditions for the red and infrared detected optical signals having optical pulses n=1, 2, and 3. However, in this transient example it is known that at n=2, the actual saturation of the patient is very close to that during the steady state conditions in the Example I. In this transient example, the detected values are as follows:

For both the red and infrared signals:
  tmax(1)=1.0 secs.
  tmin(1)=1.2 secs.
  tmax(2)=2.0 secs.
  tmin(2)=2.2 secs.
  tmax(3)=3.0 secs.
  tmin(3)=3.2 secs.
For the red optical signals:
  Vmaxr(1)=1.022 v
  Vminr(1)=1.008 v
  Vmaxr(2)=1.012 v
  Vminr(2)=0.998 v
  Vmaxr(3)=1.002 v
  Vminr(3)=0.988 v
For the infrared optical signals:
  Vmaxi(1)=1.002 v
  Vmini(1)=0.992 v
  Vmaxi(2)=1.012 v
  Vmini(2)=1.002 v
  Vmaxi(3)=1.022 v
  Vmini(3)=1.012 v Calculating the oxygen saturation ratio R at n=2, using the detected optical signals provides the following:

$$R = \ln[Vmaxr(2)/Vminr(2)]/\ln[Vmaxi(2)/Vmini(2)]$$
$$= \ln[1.012/.998]/\ln[1.012/1.002]$$
$$= .01393/.0099$$
$$= 1.4$$

Thus, the determined saturation ratio R of 1.4 based on the detected transmittance corresponds to a calculated oxygen saturation of about 51% for the patient, which corresponds to severe hypoxia in an otherwise healthy patient. This contrasts with the known saturation of about 81% and demonstrates the magnitude of the under-estimation of the oxygen saturation (over-estimation of desaturation) due to the distortion in transmittance of the red and infrared light caused by transient conditions.

Applying the preferred embodiment of the present invention to correct the distorted minimum transmittance point of the detected red optical signal during the transient condition, we find the following:

$$Vminr(2)^* = Vmin(2) + [Vmin(2) -$$
$$Vmin(1)] \times \frac{[tmax(2) - tmin(1)]}{[tmin(2) - tmin(1)]}$$
$$= 1.008 + [.998 - 1.008] \times [2.0 - 1.2]/[2.2 - 1.2]$$
$$= 1.0$$

and correspondingly for the minimum transmittance of the detected infrared optical signal we find:

$$Vmini(2)^* = .992 + [1.002 - .992] \times .8$$
$$= 1.0$$

Thus, by replacing Vminr(n) with Vminr(n)* and replacing Vmini(n) with Vmini(n)* in the calculations for determining oxygen saturation ratio R we find:

$$R = \ln[Vmaxr(2)/Vminr(2)^*]/\ln[Vmaxi(2)/Vmini(2)^*]$$
$$= \ln[1.012/1.0]/\ln[1.012/1.0]$$
$$= 1.0.$$

Thus, basing the saturation calculations on the corrected minimum transmittance values and the detected maximum transmittance values, the corrected R value corresponds to the same R for the steady state conditions and the actual oxygen saturation of the patient.

EXAMPLE V

FIGS. 7e and 7f also correspond to representative plethysmographic waveforms for a patient during increasing saturation transient conditions for the red and infrared detected optical signals having optical pulses n=1, 2, and 3. However, in this transient example it is known that at n=2, the actual saturation of the patient is identical to that during the conditions in the steady state example. In this transient example, the detected values are as follows:

For both the red and infrared signals:
  tmax(1)=1.0 secs.
  tmin(1)=1.2 secs.

tmax(2)=2.0 secs.
tmin(2)=2.2 secs.
tmax(3)=3.0 secs.
tmin(3)=3.2 secs.

For the red optical signals:
Vmaxr(1)=1.002 v
Vminr(1)=0.992 v
Vmaxr(2)=1.012 v
Vminr(2)=1.002 v
Vmaxr(3)=1.022 v
Vminr(3)=1.012 v For the infrared optical signals:
Vmaxi(1)=1.022 v
Vmini(1)=1.008 v
Vmaxi(2)=1.012 v
Vmini(2)=0.998 v
Vmaxi(3)=1.002 v
Vmini(3)=0.988 v Calculating the oxygen saturation ratio R at n=2, using the detected optical signals provides the following:

$$R = \ln[Vmaxr(2)/Vminr(2)]/\ln[Vmaxi(2)/Vmini(2)]$$
$$= \ln[1.012/1.002]/\ln[1.012/.988]$$
$$= .713$$

Thus, the determined saturation R of 0.713 corresponds to a calculated oxygen saturation of about 92% for the patient which corresponds to a mildly hypoxic patient breathing room air. This contrasts with the known saturation of about 81% and demonstrates the magnitude of the over-estimation of saturation due to the distortion in transmittance of the red and infrared light caused by transient conditions.

Applying the preferred embodiment of the present invention to correct the distorted minimum transmittance point of the detected red optical signal during the transient condition we find:

$$Vminr(2)^* = Vmin(1) + [Vmin(2) - Vmin(1)] \times \frac{[tmax(2) - tmin(1)]}{[tmin(2) - tmin(1)]}$$
$$= .992 + [1.002 - .992] \times [2.0 - 1.2]/[2.2 - 1.2]]$$
$$= 1.0$$

and correspondingly for the detected infrared optical signal:

$$Vmini(2)^* = 1.008 + [.998 - 1.008] \times [.8]$$
$$= 1.010$$

Thus, by replacing Vminr(n) with Vminr(n)* and replacing Vmini(n) with Vmini(n)* in the calculations for determining oxygen saturation ratio R we find:

$$R = \ln[Vmaxr(2)/Vminr(2)^*]/\ln[Vmaxi(2)/Vmini(2)^*]$$
$$= \ln[1.012/1.00]/\ln[1.012/1.00]$$
$$= 1.0.$$

Thus, basing the saturation calculations on the corrected minimum transmittance values and the detected maximum transmittance values, the corrected R value corresponds to the same R for the steady state conditions and the actual oxygen saturation of the patient.

Circuit Tables

| REF # | CHIP | MFR PART # | Manufacturer | DESCRIPTION OF CHIP |
|---|---|---|---|---|
| FIG. 2 | | | | |
| 210 | U2 | LF442 | NATIONAL SEMICONDUCTOR | DUAL LOW POWER OP AMP |
| FIG. 3 | | | | |
| 312 | U27 | LF444 | NATIONAL SEMICONDUCTOR | QUAD JFET OP AMP |
| 312 | U28 | LP365N | NATIONAL SEMICONDUCTOR | QUAD VOLTAGE COMPARATOR |
| 310 | U27 | LF444 | NATIONAL SEMICONDUCTOR | QUAD JFET OP AMP |
| 320 | U27 | LF444 | NATIONAL SEMICONDUCTOR | QUAD JFET OP AMP |
| 330 | U44 | MP7524LN | MICROPOWER | 8-BIT DAC |
| 330 | U32 | LF444 | NATIONAL SEMICONDUCTOR | QUAD JFET OP AMP |
| 330 | U32 | LF444 | NATIONAL SEMICONDUCTOR | QUAD JFET OP AMP |
| 315 | U20 | LP365N | NATIONAL SEMICONDUCTOR | QUAD VOLTAGE COMPARATOR |
| 340 | U32 | LF444 | NATIONAL SEMICONDUCTOR | QUAD JFET OP AMP |
| 340 | U14 | DG243CJ | SILICONIX INCORPORATED | ANALOG SWITCH |
| 340 | U7 | LF444 | NATIONAL SEMICONDUCTOR | QUAD JFET OP AMP |
| 340 | U13 | LF444 | NATIONAL SEMICONDUCTOR | QUAD JFET OP AMP |
| 350 | U7 | LF444 | NATIONAL SEMICONDUCTOR | QUAD JFET OP AMP |
| 360 | U13 | LF444 | NATIONAL SEMICONDUCTOR | QUAD JFET OP AMP |
| 370 | U7 | LF444 | NATIONAL SEMICONDUCTOR | QUAD JFET OP AMP |
| 380 | U13 | LF444 | NATIONAL SEMICONDUCTOR | QUAD JFET OP AMP |

-continued
Circuit Tables

Figure 4:
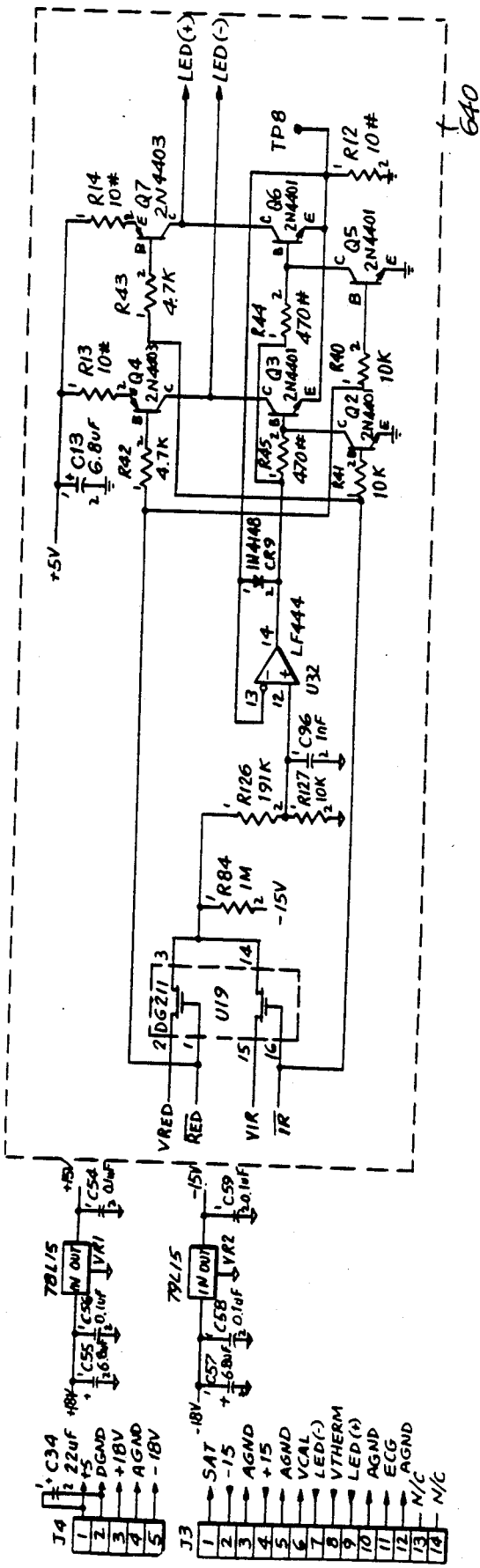
FIG. 4 is a detailed circuit schematic of the LED drive circuit of FIG. 1.

| REF # | CHIP | MFR PART # | Manufacturer | DESCRIPTION OF CHIP |
|---|---|---|---|---|
| 340 | U19 | DG211CJ | SILICONIX INCORPORATED | CMOS ANALOG SWITCH |
| FIG. 4 | | | | |
| 640 | U19 | DG211CJ | SILICONIX INCORPORATED | CMOS ANALOG SWITCH |
| 640 | U32 | LF444 | NATIONAL SEMICONDUCTOR | QUAD JFET OP AMP |
| FIG. 5 | | | | |
| 1010 | U24 | DG528CK | SILICONIX INCORPORATED | OCTAL ANALOG SWITCH |
| 1020 | U25 | LF444 | NATIONAL SEMICONDUCTOR | QUAD JFET OP AMP |
| 1030 | U25 | LF444 | NATIONAL SEMICONDUCTOR | QUAD JFET OP AMP |
| 1040 | U38 | AD7524LN | ANALOG DEVICES | DAC |
| 1040 | U42 | 74HC374 | TEXAS INSTRUMENTS | HIGH SPEED CMOS |
| 1040 | U37 | LF442N | NATIONAL SEMICONDUCTOR | LOW POWER OP AMP |
| 1050 | U36 | LF398N | NATIONAL SEMICONDUCTOR | SAMPLE & HOLD OP AMP |
| 1060 | U29 | LM211P | TEXAS INSTRUMENTS | LOW OFFSET VOLTAGE COMPARATOR |
| 1080 | U43 | AD7548KN | ANALOG DEVICES | CMOS 12-BIT DAC |
| 1080 | U31 | LF411ACN | NATIONAL SEMICONDUCTOR | LOW OFFSET OP AMP |
| 1080 | U25 | LF444 | NATIONAL SEMICONDUCTOR | QUAD JFET OP AMP |
| 610 | U18 | DG528CK | SILICONIX INCORPORATED | OCTAL ANALOG SWITCH |
| 620 | U11 | LF444 | NATIONAL SEMICONDUCTOR | QUAD JFET OP AMP |
| 630 | U11 | LF444 | NATIONAL SEMICONDUCTOR | QUAD JFET OP AMP |
| FIG. 6 | | | | |
| | U2 | 82C84A-2 | NEC | CMOS 8 MHZ CLOCK GENERATOR |
| | U1 | 74HC74 | TEXAS INSTRUMENTS | HIGH SPEED CMOS |
| | U1 | 74HC74 | TEXAS INSTRUMENTS | HIGH SPEED CMOS |
| 2040 | U8 | MSM80C88RS-2 | OKI ELECTRIC | CPU 8MHZ, 125ns |
| | U3 | 74HC74 | TEXAS INSTRUMENTS | HIGH SPEED CMOS |
| | U33 | 74HC374 | TEXAS INSTRUMENTS | HIGH SPEED CMOS |
| | U9 | 74HCO4 | TEXAS INSTRUMENTS | HIGH SPEED CMOS |
| | U3 | 74HC74 | TEXAS INSTRUMENTS | HIGH SPEED CMOS |
| | U9 | 74HCO4 | TEXAS INSTRUMENTS | HIGH SPEED CMOS |
| | U19 | 74HCOO | TEXAS INSTRUMENTS | HIGH SPEED CMOS |
| | U9 | 74HCO4 | TEXAS INSTRUMENTS | HIGH SPEED CMOS |
| 2030 | U21 | MBM27C512-25 | FUJITSU LIMITED | CMOS 64K × 8 ROM |
| 2020 | U15 | DS1242 | DALLAS SEMICONDUCTOR | CMOS 32K × 8 RAM |
| | U23 | 74HC138 | TEXAS INSTRUMENTS | HIGH SPEED CMOS |
| | U17 | 74HC138 | TEXAS INSTRUMENTS | HIGH SPEED CMOS |
| | U19 | 74HCOO | TEXAS INSTRUMENTS | HIGH SPEED CMOS |
| | U19 | 74HCOO | TEXAS INSTRUMENTS | HIGH SPEED CMOS |
| | U16 | 82C51A | OKI ELECTRIC | CMOS UART |
| | U22 | MSM82C59A-2RS | OKI ELECTRIC | CMOS INTERRUPT CONTROLLER |
| 2050 | U34 | MSM82C53-2 | OKI ELECTRIC | CMOS TRIPLE TIMER |
| 2050 | U38 | MSM82C53-2 | OKI ELECTRIC | CMOS TRIPLE TIMER |
| 2050 | U9 | 74HCO4 | TEXAS INSTRUMENTS | HIGH SPEED CMOS |
| 2050 | U39 | 74HC393 | TEXAS INSTRUMENTS | HIGH SPEED CMOS |
| 2050 | U35 | D2732A | INTEL CORPORATION | 4096 × 8 ROM |
| 2050 | U40 | 74HC374 | TEXAS INSTRUMENTS | HIGH SPEED CMOS |
| 2050 | U28 | 74HC374 | TEXAS | HIGH SPEED CMOS |

-continued

| | | | Circuit Tables | |
|---|---|---|---|---|
| REF # | CHIP | MFR PART # | Manufacturer | DESCRIPTION OF CHIP |
| | | | INSTRUMENTS | |

CRMIN - CORRECT MINIMUM - ASSUMES BX CONTAINS Ymin(n)
;

```
CR1MIN:
        PUSH    AX
        PUSH    DX
        MOV     AX,PVMIN1       ;GET Ymin(N-1)
        JMP     SHORT CRMIN4
CR2MIN:
        PUSH    AX
        PUSH    DX
        MOV     AX,PVMIN2       ;GET Ymin(n-1)
CRMIN4:
        CMP     AX,BX           ;IF Ymin(n-1) = Ymin(n) RETURN
        JE      SHORT CRMIN2
        CMP     CORRSW,0
        JE      SHORT CRMIN2
        CMP     BPCTR,3         ;IF BAD PULSE COUNTER < 3, THEN A BAD PULSE
        JC      SHORT CRMIN2    ;DON'T CORRECT
        CMP     PERIOD,0
        JE      SHORT CRMIN2
        OR      AX,AX
        JZ      SHORT, CRMIN2
        CALL    CORR
CRMIN2:                                                                 Software
        POP     DX                                                      Appendix
        POP     AX
        RET
```

CORR:
;CORRECT MINIMUM - ASSUMES BX = Ymin(n) AND AX = Ymin(n-1)
;       CORRECTED       Ymin(n) = Ymin(n-1) + (t/T)*(Ymin(n) - Ymin(n-1))
;                       WHERE t = PERIOD OF MIN TO MAX, AND
;                             T = PERIOD
;

```
        CMP     AX,BX           ;Ymin(n-1) < = Ymin(n)?
        PUSH    BX              ;SAVE Ymin(n)
        PUSHF
        MOV     CL,1            ;SET DIRECTION FLAG ACCORDINGLY
        JC      SHORT CORR4
        DEC     CL
CORR4:
        CMP     DIRMIN,CL       ;DIRECTION THE SAME?
        MOV     DIRMIN,CL       ;SAVE ANYWAY
        JE      SHORT CORR5     ;SAME, CONTINUE
        POPF
        POP     BX
        JMP     SHORT CORR2     ;NOT SAME, ABANDON SHIP
CORR5:
        SUB     BX,AX           ;Ymin(n) - Ymin(n-1)
        PUSH    AX              ;SAVE Ymin(n-1)
        JNF     SHORT CORR6
        NEG     BX
CORR6:
        PUSH    BX              ;SAVE :DELTA:
        MOV     AX,MAXMINPCTR
        MOV     CX,PERIOD
        MOV     BX,CX
        SUB     CX,AX           ;PERIOD - MAXMINPCTR
        JNS     SHORT CORR9
        POP     BX              ;RESULT SHOULD BE POSITIVE
        POP     AX
        POPF
        POP     BX              ;RESTORE ORIGINAL Ymin(n)
        JMP     SHORT CORR2
CORR9:
        CMP     CX,PERIOD       ;MUST BE LESS THAN PERIOD
        JC      SHORT CORR10
        POP     BX
        POP     AX
        POPF
        POP     BX              ;RESTORE ORIGINAL Ymin(n)
        JMP     SHORT CORR2
CORR10:
        XCHG    DX,CX           ;CX = PERIOD - MAXMINPCTR
```

-continued

```
           or         bx,bx              ;no zero divisor
           jz         cr10a
           cmp        bx,bx              ;dx must be ( bx
           jbe        cr10a
           xor        ax,ax
           div        bx                 ;CX = (PERIOD - MAXMINPCTR)/PERIOD
           mov        cx,ax              ;save result in cx
           jmp        short cr10b
cr10a:
           mov        cx,0f fffh
cr10b:
           POP        AX                 ;GET :DELTA:
           XOR        DX,DX
           MUL        CX
           OR         AH,AH
           JNS        SHORT CORR8
           INC        DL
CORR8:
           ;DX = (t/T)*: DELTA:
           POP        AX                 ;GET ORIGINAL Ymin(n−1)
           POPF
           JC         SHORT CORR7
           NEG        DX
CORR7:
           ADD        AX,DX              ;Ymin(n−1) + [(t/T)*(Ymin(n) - Ymin(N−1))]
           POP        BX                 ;DISGARD ORIGINAL Ymin(n)
           MOV        BX,AX
CORR2:
           RET
```

We claim:

1. Apparatus for compensating distortion in transmittance caused by transient conditions in a patient's plethysmograph waveform having a first and second optical signals corresponding to the transmittance of first and second light frequencies passing through the patient's tissue including arterial pulsatile blood flow for use in an oximeter device comprising:

first means for detecting periodic transmittance changes of the first frequency corresponding to the pulsatile blood flow from the first optical signal including a first maximum and minimum transmittance and a second maximum and minimum transmittance following the first maximum and minimum;

second means for detecting periodic transmittance changes of the second frequency corresponding to pulsatile blood flow from the second optical signal including a first maximum and minimum transmittance and a second maximum and minimum transmittance following the first maximum and minimum; and, for each of the first and second optical signals;

means for determining the rate of change in transmittance from one detected transmittance point of one pulse to the corresponding transmittance point of the other pulse; and processing means for adjusting one of the detected maximum or minimum transmittance values of one of the first or second pulses using the determined rate of change.

2. The apparatus of claim 1 wherein the means for determining the rate of change further comprises using linear interpolation based on the maximum or minimum transmittance of one of the first or second pulses and the occurrence of the maximum or minimum transmittance value of the other pulse.

3. The apparatus of claim 2 further comprising:

first and second digitizing means for digitizing the first and second detected optical signals, and wherein the first and second means for detecting periodic maximums and minimums and the first and second rate determining means and processing means further comprise a digital microprocessor.

4. The apparatus of claim 3 wherein the means for adjusting one of the detected maximum or minimum transmittance values of one of the first or second pulses further comprises means for selecting one of the maximum or minimum transmittance values of the first pulse to be adjusted.

5. The apparatus of claim 4 wherein the digital microprocessor further comprises means for adjusting one of the first maximum or minimum transmittance values by application of the following algorithm:

$$V(n)^* = V(n) - [V(n) - V(n+1)] \frac{[tx(n) - tn(n)]}{[tx(n+1) - tx(n)]}$$

wherein $V(n)^*$ is the adjusted maximum or minimum transmittance; $V(n)$ is the determined maximum or minimum transmittance to be adjusted; $tx(n)$ is the time of occurrence of the detected maximum or minimum transmittance to be adjusted; $tn(n)$ is the time of occurrence of the other of the detected maximum or minimum transmittance to be adjusted; and $tx(n+1)$ is the time of occurrence of the second maximum or minimum transmittance that corresponds to the first maximum or minimum transmittance to be adjusted.

6. The apparatus of claim 5 further comprising means for calculating oxygen saturation using the first and second corrected maximum or minimum transmittances and the other of the detected maximum or minimum transmittances of the first pulses for each of the first and second optical signals.

7. The apparatus of claim 3 wherein the means for adjusting one of the detected maximum or minimum transmittance values of one of the first or second pulses further comprises means for selecting one of the maximum or minimum transmittance values of the second pulse to be adjusted.

8. The apparatus of claim 7 further comprising means for calculating oxygen saturation using the first and second corrected maximum or minimum transmittances and the other of the detected maximum or minimum transmittances of the second pulses for each of the first and second optical signals.

9. The apparatus of claim 3 wherein the digital microprocessor further comprises means for adjusting one of the first maximum or minimum transmittance values by application of the following algorithm:

$$V(n)^* = V(n-1) + [V(n) - V(n-1)] \times \frac{[tx(n) - tn(n-1)]}{[tn(n) - tn(n-1)]}$$

wherein $V(n)^*$ is the adjusted maximum or minimum transmittance; $V(n)$ is the determined maximum or minimum transmittance to be adjusted; $tx(n)$ is the time of occurrence of the detected maximum or minimum transmittance to be adjusted; $tn(n)$ is the time of occurrence of the other of the detected maximum or minimum transmittance to be adjusted; and $tn(n-1)$ is the time of occurrence of the first maximum or minimum transmittance that corresponds to the second maximum or minimum transmittance to be adjusted.

10. A method for detecting and processing arterial pulses of a patient during transient conditions comprising:
    passing a first light frequency through the patient's tissue and detecting a first optical signal corresponding to changes in the transmittance of the first frequency including periodic transmittance changes related to the patient's beating heart, aperiodic transmittance changes unrelated to the beating heart, background transmittance, and transient background transmittance changes at frequencies below the heart rate;
    passing a second light frequency through the patient's tissue and detecting a second optical signal corresponding to changes in the transmittance of the second frequency including periodic transmittance changes related to the patient's beating heart, aperiodic transmittance changes unrelated to the beating heart, background transmittance, and transient background transmittance changes at frequencies below the heart rate; and for each of the first and second detected optical signals;
    processing the detected optical signal to detect a first maximum and minimum transmittance corresponding to a periodic change related to the heartbeat and a second maximum and minimum transmittance corresponding to a following periodic change related to a following heartbeat;
    determining the rate of change in transmittance from one detected transmittance point of one pulse to the corresponding transmittance point of the other pulse; and
    adjusting one of the detected maximum or minimum transmittance values of one of the first or second pulses using the determined rate of change.

11. The method of claim 10 wherein for each of the first and second detected optical signals, adjusting the maximum or minimum transmittance by determining the rate of change further comprises using linear interpolation based on the maximum and minimum transmittance of one of the first or second pulses and the occurrence of the maximum or minimum of the other pulse.

12. The method of claim 2 wherein adjusting one of the maximum or minimum transmittance values of one of the first or second pulses further comprises selecting one of the maximum or minimum transmittance values of the first pulse to be adjusted.

13. The method of claim 12 wherein adjusting the selected maximum or minimum transmittance value further comprises applying the following algorithm:

$$V(n)^* = V(n) - [V(n) - V(n+1)] \times \frac{[tx(n) - tn(n)]}{[tx(n+1) - tx(n)]}$$

wherein $V(n)^*$ is the adjusted maximum or minimum transmittance; $V(n)$ is the determined maximum or minimum transmittance to be adjusted; $tx(n)$ is the time of occurrence of the detected maximum or minimum transmittance to be adjusted; $tn(n)$ is the time of occurrence of the other of the detected maximum or minimum transmittance to be adjusted; and $tx(n+1)$ is the time of occurrence of the second maximum or minimum transmittance that corresponds to the first maximum or minimum transmittance to be adjusted.

14. The method of claim further comprising calculating oxygen saturation of the patient's arterial blood flow using the adjusted first maximum or minimum transmittance and the other of the detected first maximum or minimum transmittance for each of the first and second optical signals.

15. The method of claim 11 wherein adjusting one of the maximum or minimum transmittance values of one of the first or second pulses further comprises selecting one of the maximum or minimum transmittance values of the second pulse to be adjusted.

16. The method of claim 15 wherein adjusting the selected maximum or minimum transmittance value further comprises applying the following algorithm:

$$V(n)^* = V(n-1) + [V(n) - V(n-1)] \times \frac{[tx(n) - tn(n-1)]}{[tn(n) - tn(n-1)]}$$

wherein $V(n)^*$ is the adjusted maximum or minimum transmittance; $V(n)$ is the determined maximum or minimum transmittance to be adjusted; $tx(n)$ is the time of occurrence of the detected maximum or minimum transmittance to be adjusted; $tn(n)$ is the time of occurrence of the other of the detected maximum or minimum transmittance to be adjusted; and $tn(n-1)$ is the time of occurrence of the first maximum or minimum transmittance that corresponds to the second maximum or minimum transmittance to be adjusted.

17. The method of claim 16 further comprising calculating oxygen saturation of the patient's arterial blood flow using the adjusted second maximum or minimum transmittance and the other of the detected second maximum or minimum transmittance for each of the first and second optical signals.

* * * * *